United States Patent [19]

Sullivan et al.

[11] Patent Number: 4,841,140
[45] Date of Patent: Jun. 20, 1989

[54] REAL-TIME COLOR COMPARATOR

[75] Inventors: Charles T. Sullivan; J. David Zook, both of Burnsville, Minn.

[73] Assignee: Honeywell Inc., Minneapolis, Minn.

[21] Appl. No.: 118,587

[22] Filed: Nov. 9, 1987

[51] Int. Cl.⁴ .............................................. G01J 3/50
[52] U.S. Cl. .................................. 250/226; 250/227; 356/328
[58] Field of Search ...................... 250/226, 227, 578; 356/219, 326, 328

[56] References Cited

U.S. PATENT DOCUMENTS

| | | |
|---|---|---|
| 2,046,958 | 7/1936 | Marvin . |
| 3,690,771 | 9/1972 | Armstrong et al. . |
| 3,834,817 | 9/1974 | Vinnemann et al. . |
| 4,076,421 | 2/1978 | Kishner . |
| 4,135,820 | 1/1979 | Drews et al. . |
| 4,176,957 | 12/1979 | Maeda et al. ............. 356/319 |
| 4,185,191 | 1/1980 | Stauffer . |
| 4,230,941 | 10/1980 | Stauffer . |
| 4,249,073 | 2/1981 | Stauffer et al. . |
| 4,250,376 | 2/1981 | Joseph et al. . |
| 4,254,330 | 3/1981 | Stauffer et al. . |
| 4,275,963 | 6/1981 | Primbsch . |
| 4,291,975 | 9/1981 | Raccah . |
| 4,333,007 | 6/1982 | Langlais et al. . |
| 4,425,501 | 1/1984 | Stauffer ...................... 250/578 |
| 4,718,764 | 1/1988 | Fink ............................ 356/328 |
| 4,756,619 | 7/1988 | Gerlinger et al. ........... 356/328 |

FOREIGN PATENT DOCUMENTS

| | | | |
|---|---|---|---|
| 56-119822 | 9/1981 | Japan ......................... 356/328 |
| 7905871 | 2/1981 | Netherlands .................. 356/328 |

OTHER PUBLICATIONS

Norman Stauffer & Denny Wilwerding, "Electronic Focus for Cameras", Scientific Honeyweller, vol. 3, No. 1, Mar. 1982, pp. 1–13.

Primary Examiner—Edward P. Westin
Assistant Examiner—Khaled Shami
Attorney, Agent, or Firm—O. Richard Dahle

[57] ABSTRACT

A real-time color comparator which performs color comparisons of sample objects to a reference color for the purpose of identification, sorting or matching. Two optical paths are positioned to collect the light from a reference object and a sample object and the light outputs from the two paths are directed onto a spherical dispersive element shown in the form of a concave diffraction grating that decomposes each light signal into its spectral constituents which are imaged on a dual photodetector array. The color signature from the reference and the color signature from the sample are compared.

9 Claims, 3 Drawing Sheets

REAL-TIME COLOR COMPARATOR

BACKGROUND AND SUMMARY OF THE INVENTION

This invention is directed to the field of real-time color comparators which performs color comparison of sample objects to reference colors for the purpose of identification, sorting or matching.

Manufacturing and process automation sometimes require the determination of whether a colored sample matches that of a colored reference. For example, if the reference color represents the desired output characteristic of a continuous process (e.g., paint mixing, chemical reactions, baking), the real-time color comparator can be used as an endpoint detector for the process.

In the present invention use is made of spectral reflectance distributions of sample versus reference colors, that is, the colors per se are compared indirectly. In the present invention a reference color object and a sample object are similarly illuminated. Two optical paths are positioned to observe the reference object and the sample object; in the embodiment disclosed separate optical fibers are utilized, a reference fiber to observe the reference object and a sample fiber to observe the sample object. The outputs from the two fibers are directed onto a spectral dispersive element shown in the form of a concave diffraction grating that decomposes each light signal into its spectral constituents which are imaged on a photodetector array. Photodiodes in the array generate an analogue signal which represents the color signature of the object. The color signature from the reference and the color signature from the sample are compared.

DESCRIPTION

Figure 1:
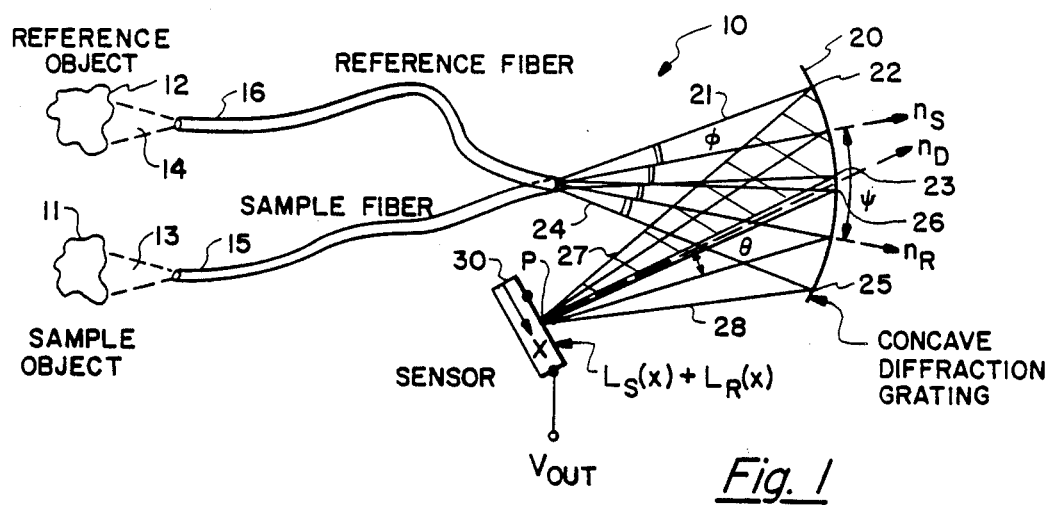
FIG. 1 of the drawing is a diagrammatic presentation of an embodiment of the invention.

Referring now to the drawing there is shown generally at 10 a color signature sensor in which it is desired to compare the color of a sample object 11 with the color of a reference object 12. The objects 11 and 12 are given illumination which is similar. Color perception depends on the spectral energy density of the illumination source, the spectral reflectance distribution of the object, and the spectral responsivity characteristics of the signal acquisition system. This invention deals only with the signal acquisition system and presupposes suitable illumination of both a reference object and a sample object.

Collecting the light signals 13 and 14 from objects 11 and 12 are two essentially identical optical fibers (a sample fiber 15 and a reference fiber 16) which route the light signals to a spectral dispersive element 20, here shown in the form of a concave diffraction grating. The concave diffraction grating is used to produce a focussed light spectrum on the input face of a detector array 30, that is, the focussed light is dispersed spectrally over the spatial extent of the acceptance aperture of array 30.

Figure 2:
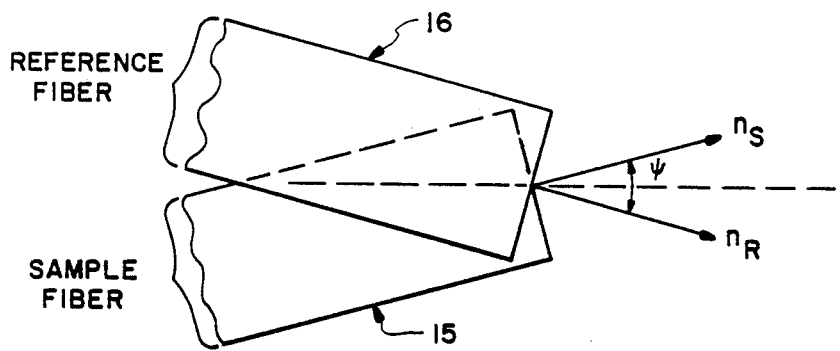
FIG. 2 shows an enlargement of the optical fibers at the output end where the end faces are flat and orthogonal to their axes.
Figure 3:
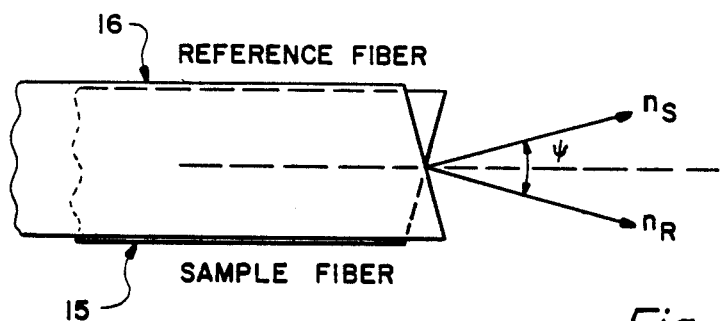
FIG. 3 is like FIG. 2 for another embodiment of the invention where the end faces are flat and nonorthogonal.

Referring back to the sample and reference fibers 15 and 16, the output ends of both fibers are placed in close proximity to each other such that: (1) referring now to FIG. 2 for flat, orthogonal end-faces, the axis $n_R$ of the radiation pattern of the reference fiber 16 coincides with the physical axis of 16 and is oriented at an angle $\psi$ with respect to the axis $n_S$ of the radiation pattern of the sample fiber 15 (coinciding with the physical axis of 15) such that $\psi > 2\phi$, where $\phi$ is the far-field half-angle encompassing the cone of light radiating symmetrically about each fiber axis, or (2) referring now to FIG. 3 for flat, nonorthogonal end-faces, both fiber physical axes are parallel, but each end-face is oriented (via rotation about the fiber physical axis) in the opposite sense, such that each cone of light described by the radiation pattern axes $n_R$ and $n_S$ radiates on different sides of their common axis. With this arrangement the emerging cone of light 21 from the sample fiber 15 impinges concave diffraction grating 20 over the area from 22 to 23, and the emerging cone of light 24 from reference fiber 16 impinges the grating over the area from 25 to 26. The concave diffraction grating 20 images each fiber end-face spot to a sensor 30 output spot P (for monochromatic light) and spectrally disperses it across the length of the sensor input (for polychromatic light). Thus for the monochromatic light shown in FIG. 1, the light 21 from the sample fiber which impinges on grating 20 is diffracted back 27 to point P on the sensor 30 and similarly the light 24 from the reference fiber which impinges on grating 20 is diffracted back 28 to point P on the sensor 30. The total integrated light intensity at any point P at the sensor input plane is given as $L(P) = L_S(P) + L_R(P)$, where the spectrally dispersed light signal $L_S$ from 11 arrives at an angle $\theta < 0$ (referenced to the sensor normal axis $n_D$) and the spectrally dispersed light signal $L_R$ from 12 arrives at an angle $\theta > 0$ as shown. The sensor compares the light intensity versus space distribution (i.e., also spectrally dispersed) of $L(\theta > 0) = L_R$ to $L(\theta < 0) = L_S$ and outputs a voltage related to their similarity. An example of such a distributed sensor which outputs a measure of similarity is the Honeywell Through-the-Camera-Lens (TCL) chip (disclosed in such U.S. patent documents as U.S. Pat. No. 4,333,007 6/82 Langlais et al; 4,254,330 3/81 Stauffer et al; 4,250,376 2/81 Joseph et al; 4,249,073 2/81 Stauffer et al, 4,230,941 10/80 Stauffer, and 4,185,191 1/80 Stauffer, all assigned to the same assignee as the present invention). In the case of the TCL chip, as disclosed and used in the named patents, the measure of similarity is the normal autofocus output signal which indicates the amount of lens movement necessary to produce a proper focus condition; no lens movement is required when the similarity condition is established by prior lens movements. In this present invention the output signal indicating similarity can be used rather for the purpose of color matching. Explicitly, when $L_S(\lambda)$ and $L_R(\lambda)$ are determined by the sensor to be sufficiently similar, the sample and reference colors are said to match. Similarly, when $L_S(\lambda)$ and $L_R(\lambda)$ are determined by the sensor to be sufficiently dissimilar, the sample and reference colors are said to not match. Since both $L_S(\lambda)$ and $L_R(\lambda)$ are characteristic light distributions from illuminated, colored objects, the sensor compares two object colors in real-time. This color comparison is indirect since the object colors per se are not determined in any case; however, this color comparison is correct and sufficient, limited primarily by the physical structure and precision of the sensor.

Figure 4:
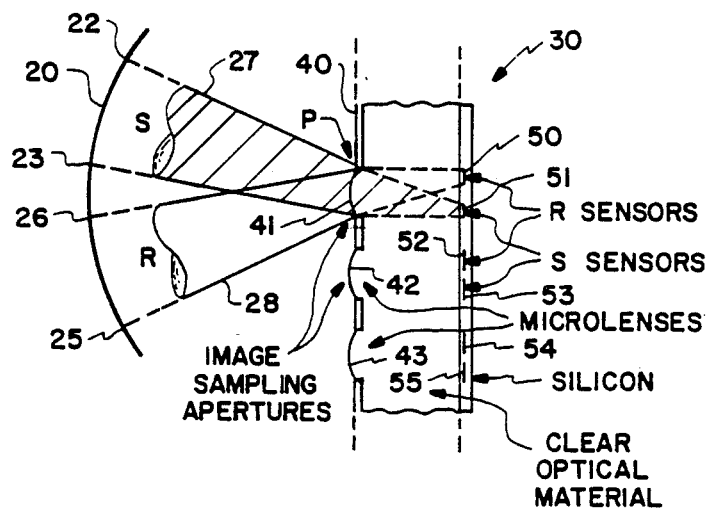
FIG. 4 shows an enlargement of a portion of the sensor structure of FIG. 1.

Referring now to FIG. 4, which is an exemplary embodiment of the TCL chip there is shown in more detail the nature of three sensors of the sensor array 30. The light 27 and 28 from the grating 20 falls on the surface 40 of the sensor array chip. On this surface are tiny microlenses 41, 42 and 43. Associated with each of the microlenses are two detectors. Each lens projects an image of the received light on two of the detector layers 50–55 in which detectors 50, 52 and 54 are identified as R sensors (that is reference sensors) and in which detectors 51, 53 and 55 are identified as S sensors (that is sample sensors). Each of the R sensors receives light from the 25,26 sector of grating 20 and each of the S sensors receives light from the 22,23 sector of the grating. In all there are 24 microlenses and 24 pairs of detectors in a linear array about 5 millimeters long. Unwanted light is precluded by an aperture mask above the lenslet array.

Figure 5:
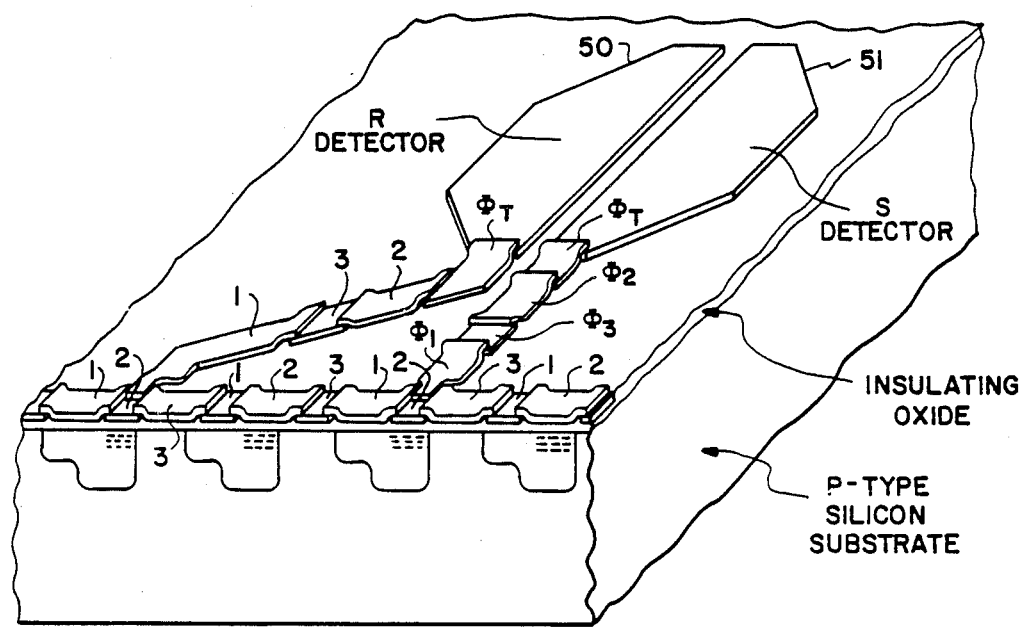
FIG. 5 shows an enlargement of a portion of FIG. 4.

In FIG. 5 is shown a cutaway of the sensor chip previously described showing one pair of detectors, such as 50 and 51, and the shift register circuitry which transfers charge packets from the detectors to output circuitry. A sensor array of this type is also described in greater detail in an article by Norm Stauffer and Denny Wilwerding entitled "Electronic Focus for Cameras", Scientific Honeyweller, Volume 3, Number 1, March 1982, pages 1-13 from which FIG. 5 is taken.

Figure 6:
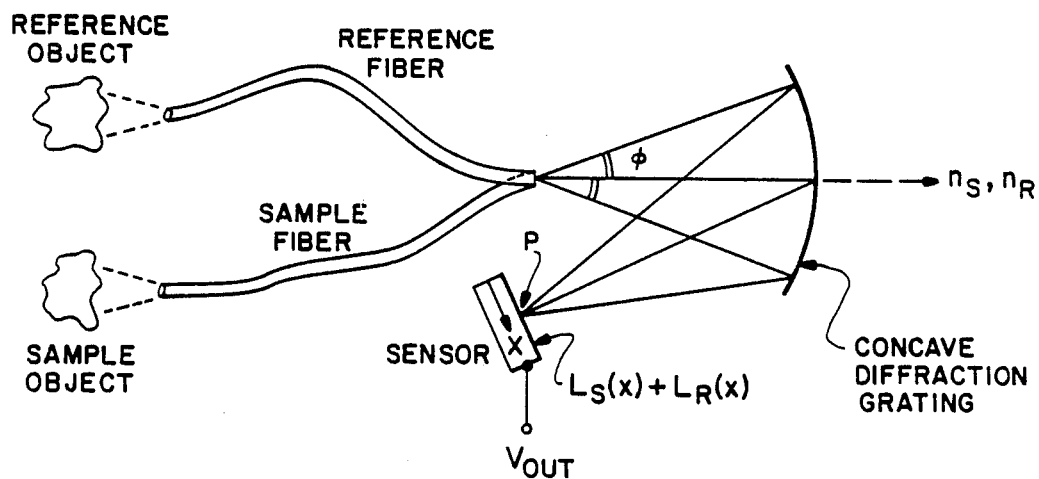
FIG. 6 shows another embodiment of the real-time color comparator.

Referring now to FIG. 6 there is shown an alternative embodiment of FIG. 1 that is produced by requiring $\psi=0$ in FIG. 1. In terms of the descriptors of FIG. 1, FIG. 6 requires that the area of impingement from 22 to 23 of the sample core of light 21 is essentially identical to the area of impingement from 26 to 25 of the reference core of light 24. In this embodiment, the sample fiber 15 and the reference fiber 16 have flat, orthogonal end-faces that are placed in close proximity in such a way their physical axes are parallel to one another. Since the physical axes of the sample fiber 15 and the reference fiber 16 are not coincident, they appear as distinct disks of light that are imaged by the concave diffraction grating 20 into distinct disks of light on the input face of the sensor. The physical separation of the focussed light signals on the sensor face permits at least two different ways of acquiring the spectrally and spatially dispersed light distributions.

Figure 7:
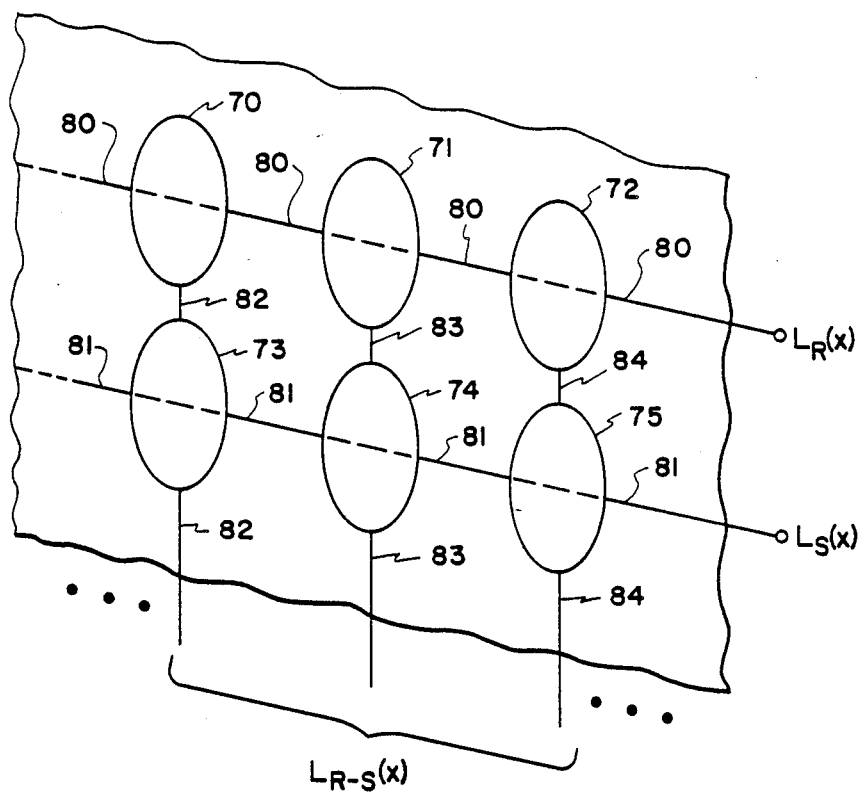
FIG. 7 shows an enlargement of the sensor aperture of the embodiment of FIG. 6.

Referring now to FIG. 7 there is shown in more detail the sensor aperture that can detect the physically separated, spectrally and spatially dispersed light distributions $L_S(x)$ and $L_R(x)$. In FIG. 7 apertures 70–75 can be considered for simplicity to represent detectors as well. The spectrally dispersed light signal $L_R(x)$ is an output of a series of detectors exemplified by 70, 71 and 72 and interconnected by the appropriate circuitry and wiring 80. Similarly, the spectrally dispersed light signal $L_S(x)$ is an output of another series of detectors exemplified by 73, 74 and 75 and interconnected by the appropriate circuitry and wiring 81. The physical arrangement to produce orderly imaging and spectral dispersion in the sensor plane of FIG. 7 is such that the adjacent detector pairs (70,73), (71,74) and (72,75) have adjacent, quasi-monochromatic light impinging on them, but both elements of every pair experience and detect precisely the same wavelength bands. The signal outputs from 80 and 81 can be processed in real-time in any appropriate manner to obtain a measure of similarity between $L_R(x)$ and $L_S(x)$. Example measures of similarity are signature cross-correlation and mean-value difference as disclosed by Sullivan under the copending application Ser. No. 118,585, filed Nov. 9, 1987, and assigned to the same assignee as the present invention.

Alternatively, the exemplary circuitry and wiring 82, 83 and 84 can be configured to obtain a measure of similarity between 70 and 73, 71 and 74, and 72 and 75, respectively. A simple example of similarity between these successive detector pairs is an element-by-element subtraction to obtain a new signal $L_{R-S}(x)$ that represents effectively a color signature difference.

This simultaneous, two-dimensional sensing of spatially dispersed light distributions can be extended to include several reference signals and/or several sample signals for color matching or sorting purposes.

The two fibers 15 and 16 have been shown without any auxiliary input or output lenses. Additional optical lenses may be optionally used such as positioned between object and fiber to affect collection efficiency, angle of view and the like.

The embodiments of the invention in which an exclusive property or right is claimed are defined as follows:

1. Input mechanism to a color comparator apparatus comprising:

first optical path means having an input end and an output end, said input end being adapted to collect and transmit the color of a reference object to said output end;

second optical path means having an input end and an output end, said input end being adapted to collect and transmit the color of a sample object to said output end;

spectral dispersive element means in the form of a single concave diffraction grating, said grating including a reference area and a sample area which are spatially separated one from the other on said concave diffraction grating;

means positioning said first optical path means output end to direct reference light emanating therefrom to the reference area on said concave diffraction grating;

means positioning said second optical path means output end to direct sample light emanating therefrom to the sample area on said concave diffraction grating;

a photodetector array, said photodetector array having a reference linear array of photodetectors and adjacent thereto a sample linear array of photodetectors;

means directing diffracted light from said reference area onto said reference linear array of photodetectors from a first solid angle and directing diffracted light from said sample area onto said sample linear array of photodetectors from a different solid angle, said reference array and sample array of photodetectors producing a plurality of light intensity signals representative of the spectral distribution of the reference object color and the sample object color.

2. The apparatus according to claim 1 and further comprising comparator means for simultaneously receiving the plurality of light intensity signals from the reference linear array and from the sample linear array and subtracting said signals for direct spectral component comparison.

3. The apparatus according to claim 1 in which said first and second optical path means comprise first and second optical fibers respectively.

4. The apparatus according to claim 1 in which said means directing diffracted light from said reference area onto said reference linear array and directing diffracted light from said sample area onto said sample linear array comprises a plurality of linear apertures with one of said reference photodetectors and one of said sample photodetectors of said reference linear array and of said sample linear array behind each aperture.

5. The apparatus according to claim 4 and further comprising comparator means for simultaneously receiving the plurality of light intensity signals from the reference linear array and from the sample linear array and subtracting said signals for direct spectral component comparison.

6. The apparatus according to claim 1 in which said means positioning comprise the output ends of said first and second optical path means being placed in close proximity to each other and oriented such that the axis $n_R$ of the light cone emanating from the first optical path means is oriented at an angle with respect to the axis $n_S$ of the light cone emanating from the second optical path means such that $\psi \geq 2\phi$, where $\phi$ is the far-field half-angle encompassing the cone of light diffracting about each axis $n_R$ and $n_S$.

7. Real-time color comparator apparatus comprising:
a reference optical fiber having an input end and an output end, said input end being adapted to observe and transmit the color of a reference object;
a sample optical fiber having an input end and an output end, said input end being adapted to observe and transmit the color of a sample object;
a single concave diffraction grating;
means positioning said reference fiber output end to direct light emanating from the output end of said reference optical fiber to a first reference area on said concave diffractive grating;
means positioning said sample fiber output end to direct sample light emanating therefrom to a second sample area on said concave diffraction grating, the second sample area being spatially separated from said first reference area on said concave grating;
a photodetector array, said photodetector array having a reference linear array of photodetectors and a sample linear array of photodetectors;
means focussing diffracted light from said first reference area onto said reference linear array of photodetectors and focussing diffracted light from said second sample area onto said sample linear array of photodetectors, said reference array and sample array of photodetectors producing a plurality of light intensity signals representative of the spectral distribution of the reference object color and the sample object color.

8. The apparatus according to claim 7 and further comprising comparator means for simultaneously receiving the plurality of light intensity signals from the reference linear array and from the sample linear array and subtracting said signals to get a difference between reference and sample for direct spectral component comparison.

9. The apparatus according to claim 7 in which said photodetector array has a plurality of linear apertures with one reference photodetector and one sample photodetector of said reference linear array and of said sample linear array behind each aperture.

* * * * *